US012693302B2

(12) United States Patent
Mussman et al.

(10) Patent No.: US 12,693,302 B2
(45) Date of Patent: Jul. 28, 2026

(54) SYSTEM INCLUDING AUTONOMOUS PARTICULATE PROBE ASSEMBLY, AND RELATED METHODS AND COMPUTER-READABLE MEDIUM

(71) Applicant: The GSI Group, LLC, Assumption, IL (US)

(72) Inventors: Adam Thomas Mussman, Assumption, IL (US); Liang Shang, Assumption, IL (US); Lance Brown, Assumption, IL (US); Lonny Sund, Omaha, NE (US); Jason Lowe, Omaha, NE (US); Zhong Zhou, Assumption, IL (US)

(73) Assignee: The GSI Group, LLC, Assumption, IL (US)

( * ) Notice: Subject to any disclaimer, the term of this patent is extended or adjusted under 35 U.S.C. 154(b) by 228 days.

(21) Appl. No.: 18/549,427

(22) PCT Filed: Apr. 13, 2022

(86) PCT No.: PCT/IB2022/053483
§ 371 (c)(1),
(2) Date: Sep. 7, 2023

(87) PCT Pub. No.: WO2022/219561
PCT Pub. Date: Oct. 20, 2022

(65) Prior Publication Data
US 2024/0159788 A1      May 16, 2024

Related U.S. Application Data

(60) Provisional application No. 63/174,419, filed on Apr. 13, 2021.

(51) Int. Cl.
*G01N 35/10* (2006.01)
*G01N 1/08* (2006.01)
(Continued)

(52) U.S. Cl.
CPC .............. *G01N 35/10* (2013.01); *G01N 1/08* (2013.01); *G01N 33/02* (2013.01);
(Continued)

(58) Field of Classification Search
CPC .......... G01N 35/10; G01N 1/08; G01N 33/02; G01N 35/0099; G01N 2001/1006;
(Continued)

(56) References Cited

U.S. PATENT DOCUMENTS

| | | | |
|---|---|---|---|
| 4,037,476 A | 7/1977 | McCrabb |
| 4,616,515 A | 10/1986 | Dancoine |

(Continued)

FOREIGN PATENT DOCUMENTS

| | | |
|---|---|---|
| CN | 112378697 A | 2/2021 |

OTHER PUBLICATIONS

European Patent Office, Search Report for related PCT Application No. PCT/IB2022/053483, dated Jun. 24, 2022, 12 pages.

*Primary Examiner* — Benjamin R Schmitt
(74) *Attorney, Agent, or Firm* — Ray Quinney & Nebeker

(57) ABSTRACT

An autonomous probing system includes a computer, a probe assembly, a PLC, and an optical sensor. The optical sensor captures image data of a probing environment. The probe assembly includes a moveable probe portion and a sensor. The probe portion is moveable between a first and second position. The sensor has a first sensor value that is indicative of the first position. The computer receives image data from the optical sensor and detects a vehicle positioned within the probing environment. The computer then determines one or more target areas within the vehicle and an X coordinate position and a Y coordinate position of one or more probe target points within each of the target areas. Based on the first sensor value and the X and Y coordinate positions, the computer determines a second sensor value, (Continued)

which is indicative of the second position and transmits the value to the PLC.

17 Claims, 4 Drawing Sheets

(51) Int. Cl.

| | |
|---|---|
| *G01N 33/02* | (2006.01) |
| *G01N 35/00* | (2006.01) |
| *G06T 7/00* | (2017.01) |
| *G06T 7/73* | (2017.01) |
| *G01N 1/10* | (2006.01) |

(52) U.S. Cl.

CPC ....... *G01N 35/0099* (2013.01); *G06T 7/0004* (2013.01); *G06T 7/73* (2017.01); *G01N 2001/1006* (2013.01); *G01N 2001/1037* (2013.01); *G06T 2200/24* (2013.01); *G06T 2207/30128* (2013.01); *G06T 2207/30248* (2013.01)

(58) Field of Classification Search

CPC . G01N 2001/1037; G06T 7/0004; G06T 7/73; G06T 2200/24; G06T 2207/30128; G06T 2207/30248

See application file for complete search history.

(56) References Cited

U.S. PATENT DOCUMENTS

| | | |
|---|---|---|
| 2007/0171764 A1 | 7/2007 | Klein et al. |
| 2017/0042081 A1* | 2/2017 | Zumbach ................. G01N 1/08 |
| 2019/0187046 A1 | 6/2019 | Caneda |

* cited by examiner

SYSTEM INCLUDING AUTONOMOUS PARTICULATE PROBE ASSEMBLY, AND RELATED METHODS AND COMPUTER-READABLE MEDIUM

CROSS-REFERENCE TO RELATED APPLICATIONS

This application is a national phase entry under 35 U.S.C. § 371 of International Patent Application PCT/IB2022/053483, filed Apr. 13, 2022, designating the United States of America and published in English as International Patent Publication WO WO 2022/219561A1 on Oct. 20, 2022, which claims the priority benefit of identically titled U.S. Provisional Patent Application Ser. No. 63/174,419, filed Apr. 13, 2021, the entirety of which is incorporated herein by reference.

FIELD OF THE DISCLOSURE

The embodiments described herein relate generally to a particulate probing system and, more particularly to systems and methods for autonomously probing a particulate hauling vehicle to retrieve one or more samples of the particulate therefrom.

BACKGROUND

Typically, grain handling facilities include grain probing systems to facilitate receiving, sampling, and grading a grain load. The grain probing systems, however, are generally manually controlled by an onsite or remote operator. Manual operation of the probing systems may be labor-intensive, inefficient, and slow. This can cause a backup of trucks at the grain handling facilities during peak grain receiving season. Some grain handling facilities can receive hundreds of trucks a day. Furthermore, it can be difficult to identify and/or expensive to employ competent/skilled operators.

Accordingly, an autonomous grain probing system is desirable. Such an autonomous grain probing system can facilitate the following: i) reduction of manual labor currently required in known systems; ii) increase efficiency and speed of receiving, sampling, and/or grading a grain load; and iii) extend hours of operation of grain handling facilities beyond what is currently typical (e.g., overnight and/or substantially continuous operation).

SUMMARY

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present disclosure will be apparent from the following detailed description of the embodiments and the accompanying drawing figures.

In one aspect, an autonomous system is provided. The system includes a particulate sampling probe assembly, a programmable logic controller operatively coupled to the particulate sampling probe assembly, an optical sensor that captures image data of a predefined probing environment, and a computer coupled in communication to the optical sensor, the programmable logic controller, and the particulate sampling probe assembly. The particulate sampling probe assembly includes a probe portion that is moveable between a first position and a second position, and a sensor having a first sensor value, which is indicative of the first position. The computer includes a processing element and a memory element. The memory element has computer executable instructions stored thereon that, when executed by the processing element, cause the processing element to receive the image data from the optical sensor. The processing element also detects a vehicle positioned within the predefined probing environment. Based on the image data, the processing element determines one or more target areas within the vehicle. The processing element also determines an X coordinate position and a Y coordinate position of one or more probe target points within each of the one or more target areas. The processing element retrieves the first sensor value from the sensor and determines a second sensor value based on the first sensor value and the X and Y coordinate positions. The second sensor value is indicative of the second position, which corresponds to the probe portion being positioned at one of the X and Y coordinate positions in one of the one or more target areas. The processing element also transmits the second sensor value to the programmable logic controller.

In another aspect, a method is provided. The method is performed by a computer of an autonomous system. The autonomous system includes a particulate sampling probe assembly, a programmable logic controller, and an optical sensor that captures image data of a predefined probing environment. The particulate sampling probe assembly includes a moveable probe portion that is moveable between a first position and a second position. The particulate sampling probe assembly also includes a sensor having a first sensor value, which is indicative of the first position. The method includes receiving image data from the optical sensor and detecting a vehicle positioned within the predefined probing environment. The method also includes determining one or more target areas within the vehicle based on the image data, and an X coordinate position and a Y coordinate position of one or more probe target points within each of the one or more target areas. Furthermore, the method includes retrieving the first sensor value from the sensor. In addition, the method includes determining a second sensor value based on the X and Y coordinate positions. The second sensor value is indicative of the second position, which corresponds to the probe portion being positioned at one of the X and Y coordinate positions in one of the one or more target areas. Moreover, the method includes transmitting the second sensor value to the programmable logic controller.

In yet another aspect, a non-transitory computer-readable medium is provided. The non-transitory computer-readable medium has stored thereon computer executable instructions that when executed by a processor of computer, cause the processor to perform the step of receiving image data from an optical sensor. The image data is captured of a predefined probing environment. The computer executable instructions also cause the processor to detect a vehicle positioned within the predefined probing environment and based on the image data, determine one or more target areas within the vehicle. Additionally, the computer executable instructions cause the processor to determine an X coordinate position and a Y coordinate position of one or more probe target points within each of the one or more target areas. The computer executable instructions cause the processor to retrieve a first sensor value from a sensor of a particulate sampling probe assembly. The particulate sampling probe assembly includes a moveable probe portion that is moveable between a first position and a second position. The first sensor value is indicative of the first position. The computer executable instructions also cause the processor to determine a second sensor value based on the first sensor value and the X and Y coordinate positions. The second sensor value is indicative of the second position, which corresponds to the probe portion being positioned at one of the X and Y coordinate positions in one of the one or more target areas. Moreover, the computer executable instructions cause the processor to transmit the second sensor value to the programmable logic controller.

Advantages of these and other embodiments will become more apparent to those skilled in the art from the following description of the exemplary embodiments which have been shown and described by way of illustration. As will be realized, the present embodiments described herein may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of systems and methods disclosed therein. It should be understood that each figure depicts an embodiment of a particular aspect of the disclosed systems and methods, and that each of the figures is intended to accord with a possible embodiment thereof. Further, wherever possible, the following description refers to the reference numerals included in the following figures, in which features depicted in multiple figures are designated with consistent reference numerals.

Figure 1:
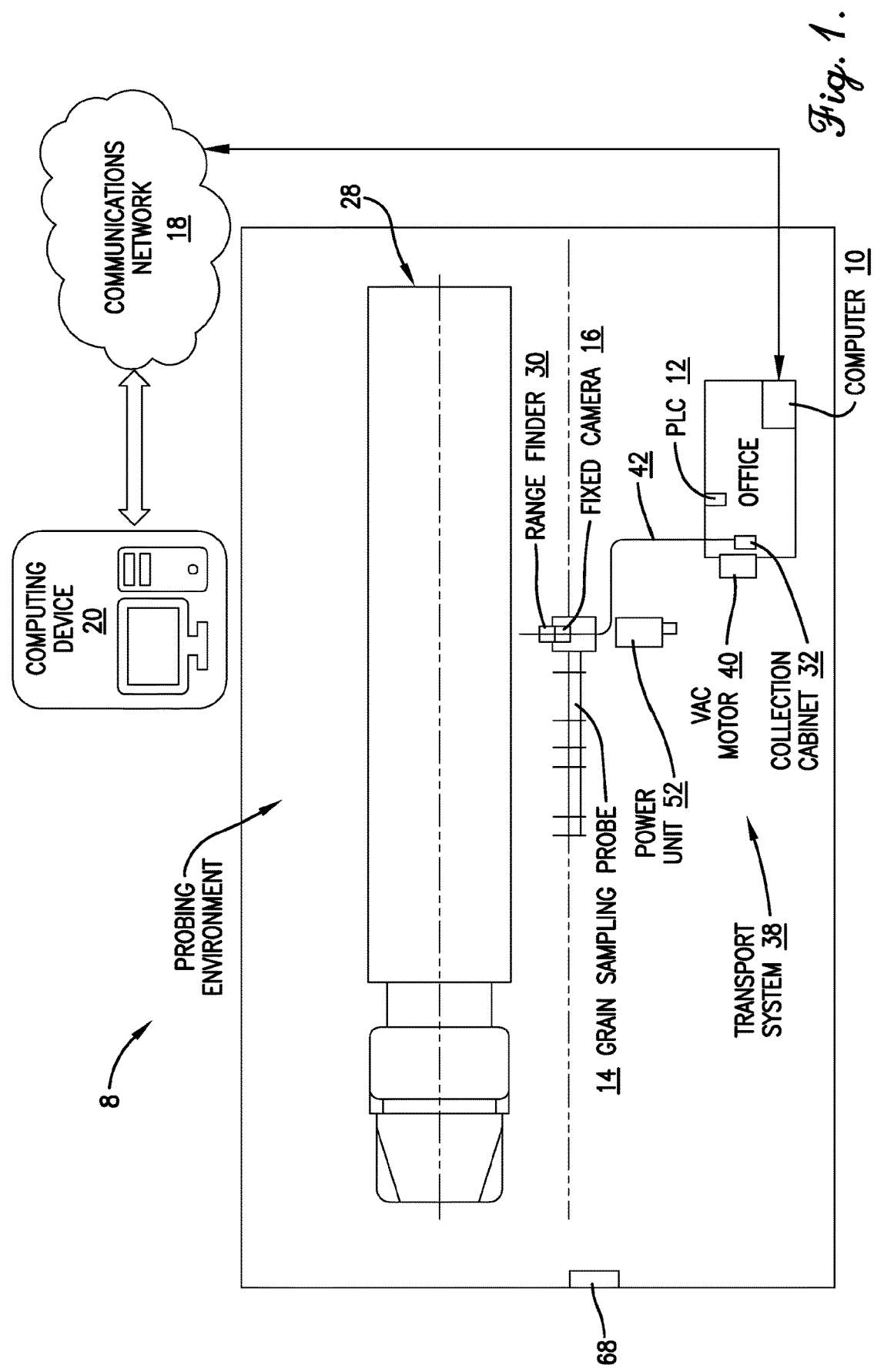
FIG. 1 depicts an exemplary autonomous grain probing system, in accordance with one aspect of the present invention.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

The following detailed description of embodiments of the invention references the accompanying figures. The embodiments are intended to describe aspects of the invention in sufficient detail to enable those with ordinary skill in the art to practice the invention. The embodiments of the invention are illustrated by way of example and not by way of limitation. Other embodiments may be utilized, and changes may be made without departing from the scope of the claims. The following description is, therefore, not limiting. The scope of the present invention is defined only by the appended claims, along with the full scope of equivalents to which such claims are entitled.

Broadly, embodiments of the present technology relate to systems, computer-readable media, and computer-implemented methods for autonomously probing a particulate hauling vehicle to retrieve one or more samples of the particulate therefrom. Embodiments of the present technology reduce or eliminate the need for a person to operate a probe to perform a probing/sampling operation. The function of the autonomous probe is to accomplish one or more of the following processes: utilize optical sensor technology to identify a type and position of a vehicle that it is capable of being probed; identify location of a particulate contained in the vehicle; locate one or more target areas of the particulate to sample; probe the particulate without damaging the vehicle or probe; automatically turn a particulate transport or transfer assembly on and off to retrieve and deliver a sample of the particulate to a hopper or other sample containment device; and, optionally, return the probe to a home position.

In addition to the optical sensor (e.g., a camera), the systems described herein may include additional sensors, such as proximity sensors for vehicle position and placement, resistance monitoring to detect probe/vehicle contact, and various sensors for tracking a position of the probe. The optical sensor and the additional sensors may be connected to a computer that interprets the data and communicates with a programmable logic controller (PLC) or programmable controller to operate a moveable probe, such as a hydraulic probe. The computer may be able to communicate with other systems such as scale automation and automatic grain grading equipment.

Specific embodiments of the technology will now be described in connection with the attached drawing figures. The embodiments are intended to describe aspects of the invention in sufficient detail to enable those skilled in the art to practice the invention. Other embodiments can be utilized, and changes can be made, without departing from the scope of the present invention. The following detailed description is, therefore, not to be taken in a limiting sense. The scope of the present invention is defined only by the appended claims, along with the full scope of equivalents to which such claims are entitled.

Exemplary System

Figure 2:
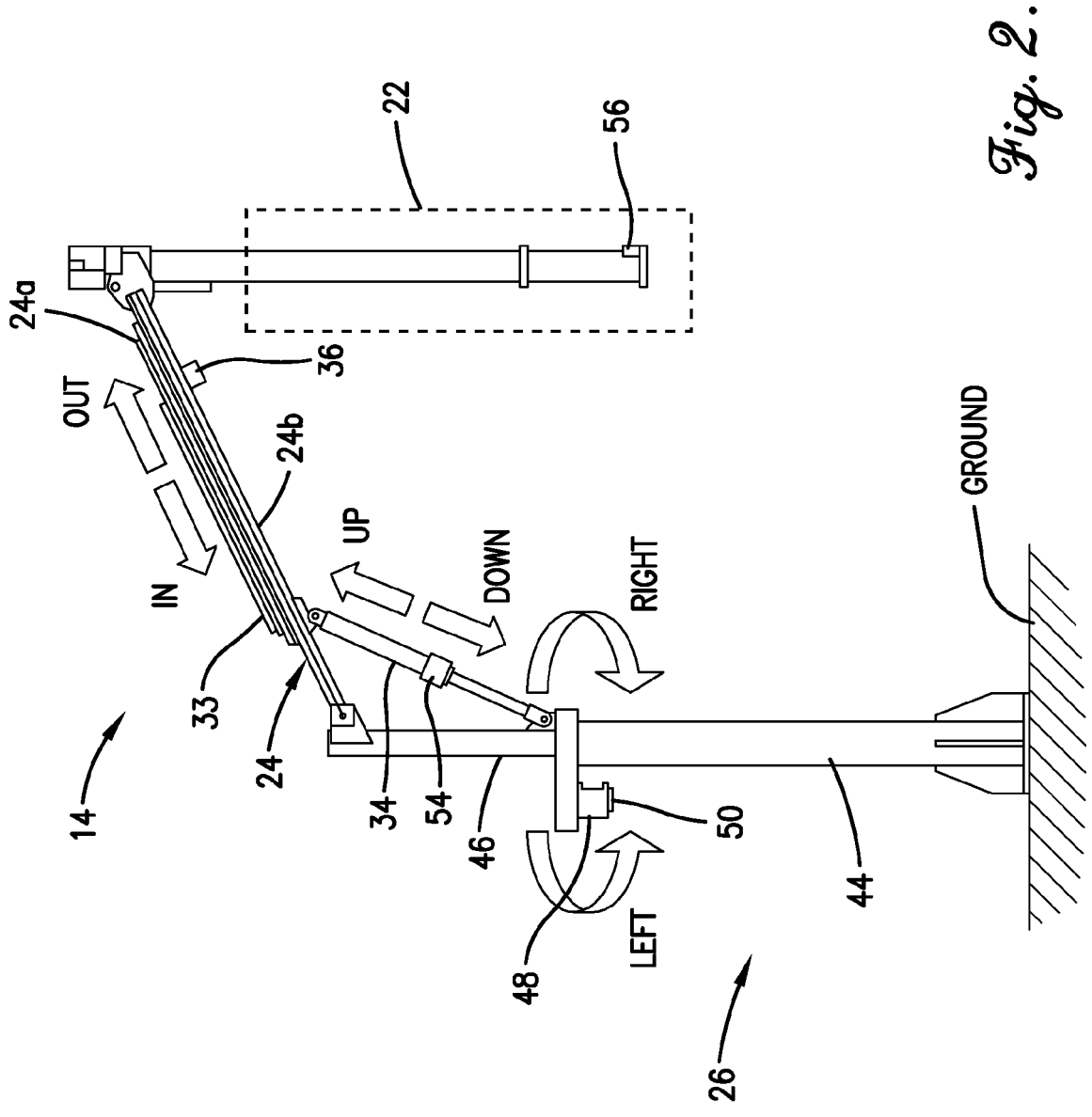
FIG. 2 is a front perspective view of an exemplary particulate sampling probe assembly shown in FIG. 1.

FIG. 1 depicts an exemplary autonomous particulate (e.g., grain) probing system 8 (broadly, an autonomous system), in accordance with an aspect of the invention. FIG. 2 is an exemplary view of a particulate (e.g., grain) sampling probe assembly 14 depicted in FIG. 1. While described herein as a grain probing system, it is noted that the probing system may be configured to sample any suitable type of particulate, including, for example, pellets, chips, flakes, granules, powders, and the like. The system 8 may include a computer 10, a programmable logic controller (PLC) 12 (broadly, a controller), the grain sampling probe assembly 14, and an optical sensor 16 (e.g., a camera) coupled together in communication. The grain sampling probe assembly 14 includes any grain sampling probe assembly that enables the autonomous grain probing system 8 to function as described herein. For example, the grain sampling probe assembly 14 may be a mast/arm assembly, an overhead gantry assembly, and the like. In the example, as depicted in FIG. 2, the grain sampling probe assembly 14 is a mast/arm type assembly. The optical sensor 16 may include a camera or other optical sensor and lens combination capable of generating a video signal and/or capturing one or more images of at least a portion of the probing environment.

In the illustrated embodiment, the grain sampling probe assembly 14 includes a moveable (or positionable) grain probe portion 22, an extendable support arm portion 24, and a base structure portion 26. The grain probe portion 22 includes, for example, one of a core probe or a compartmentalized probe. Generally, the grain probe portion 22 has a length in a range between and including about seven feet (7 ft) and about nine feet (9 ft). It is noted, however, that the length of the grain probe portion 22 can be any measure that enables the grain sampling probe assembly 14 to function as described herein. It is noted that any particulate sampling probe assembly that includes a moveable probe portion is within the scope of the present invention.

In the example, the grain probe portion 22 is coupled to a distal end of the extendable support arm portion 24 via a pivotable joint between the grain probe portion 22 and the extendable support arm portion 24. In certain embodiments, it is contemplated that the grain probe portion 22 is coupled to the distal end of the extendable support arm portion 24 at a fixed angle. In the example embodiment, the grain probe portion 22 is moveable between a home (or stowed) position and one or more sample retrieving positions.

In the example, the extendable support arm portion 24 includes a telescoping sample line 42 (see FIG. 1) that extends along the extendable support arm portion 24 to transport a sample from the grain probe portion 22 to a collection cabinet 32. Generally, the extendable support arm portion 24 includes an inner boom 24a telescopically coupled to an outer boom 24b. The extendable support arm portion 24 is extended/retracted via a linear actuator 33. In an example embodiment, the linear actuator 33 may include, for example, a hydraulic cylinder. Furthermore, in the exemplary embodiment, the extendable support arm portion 24 includes a linear displacement sensor 36. The linear displacement sensor 36 is configured to sense a position of the inner boom 24a relative to the outer boom 24b. Furthermore, the linear displacement sensor 36 is configured to provide a linear displacement measure indicative of the relative position to the computer 10, as described herein. It is noted that, in certain embodiments, the linear displacement sensor 36 may be integrated into the linear actuator 33, defining a unitary assembly.

As depicted in FIG. 1, the grain sampling probe assembly 14 includes a particulate transport system 38 or transfer assembly for transporting a particulate sample from the grain probe portion 22 to the collection cabinet 32. In the example, the particulate transport system 38 is depicted as a vacuum system that may include, for example, a two-stage by-pass tangential vacuum motor 40 to draw a vacuum in the sample line 42 of the grain sampling probe assembly 14. It is noted, however, that the particulate transport system 38 or transfer assembly may be any type of particulate transport system that enables the autonomous grain probing system 8 to function as described herein, including, for example, a conveyor system, auger system, and the like.

Referring to FIG. 2, the preferred base structure portion 26 includes a fixed base portion 44 mounted to the ground surface (e.g., a dock, concrete pad, foundation, etc.) and a pivot tube assembly 46 rotatably coupled to an upper end of the fixed base portion 44. A rotational actuator 48 is coupled to the fixed base portion 44 and the pivot tube assembly 46 to provide controlled rotation of the pivot tube assembly 46 relative to the fixed base portion 44. The base structure portion 26 also includes an angular or rotation senor 50 configured to sense a rotational displacement of the pivot tube assembly 46 relative to the fixed base portion 44. The sensor 50 is configured to provide a rotational displacement measure indicative of the relative position to the computer 10, as described herein. It is contemplated that the rotational actuator 48 and/or the sensor 50 may be positioned anywhere on the grain sampling probe assembly 14 that enables the rotational actuator 48 and/or the sensor 50 to rotationally displace and sense such displacement, respectively.

The illustrated grain sampling probe assembly 14 also includes a linear actuator 34 extending between the extendable support arm portion 24 and the pivot tube assembly 46. The linear actuator 34 is configured to pitch the extendable support arm portion 24 up and down relative to the pivot tube assembly 46. In the example, the grain sampling probe assembly 14 also includes another linear displacement sensor 54. The linear displacement sensor 54 is configured to sense a position of the extendable support arm portion 24 relative to the pivot tube assembly 46. Furthermore, the linear displacement sensor 54 is configured to provide to the computer 10 a linear displacement measure indicative of the relative position, as described herein. It is noted that, in certain embodiments, the linear displacement sensor 54 may be integrated into the linear actuator 34, defining a unitary assembly. Alternatively, in some embodiments, the grain sampling probe assembly 14 may include another angular or rotation senor configured to sense a rotational (pitch) displacement of the extendable support arm portion 24 relative to the pivot tube assembly 46 and provide such displacement measure to the computer 10. As depicted in FIG. 1, the grain sampling probe assembly 14 includes a power unit 52 for operating the linear/rotational actuators 33, 34, and 48.

In the example embodiment, the optical sensor 16 is coupled to a fixed and known location relative to the grain sampling probe assembly 14. Preferably, the optical sensor 16 is generally located directly above the base structure portion 26 of the grain sampling probe assembly 14. In one embodiment, the optical sensor 16 is positioned at a height above the ground surface in a range between and including about twenty feet (20 ft) and about thirty feet (30 ft). It is noted, however, that the mounting height of the optical sensor 16 can be any measure that enables the grain sampling probe assembly 14 to function as described herein. Furthermore, the camera is coupled in communication to the computer 10, for example, via a wireless or wired connection.

In certain embodiments, the autonomous grain probing system 8 may optionally include a range finder 30. The range finder 30 may be positioned in a known, fixed location relative to the grain sampling probe assembly 14. For example, in one alternative embodiment, the range finder 30 may be positioned next to the optical sensor 16. In one embodiment, the range finder 30 may include a light detection and ranging (LIDAR) device. A LIDAR device can estimate distance to environmental features, such as a surface of a product to be sampled in a trailer. In general, a LIDAR device scans a scene by transmitting a laser pulse and detecting a returning pulse, if any, reflected from an object in the environment. The LIDAR device determines the distance to the object according to a time delay between the transmitted pulse and reception of a reflected pulse. A LIDAR device may include, for example, a laser or set of lasers, and may rapidly and repeatedly scan across a scene to provide continuous real-time information on distances to reflective objects in the scene. Combining the measured distances and the orientation of the laser(s) while measuring distance allows for associating a three-dimensional position with each returning pulse.

Referring back to FIG. 1, the grain sampling probe assembly 14 is generally configured, for example, to capture a particulate sample from a particulate load transported to a facility by a vehicle 28, such as a truck or trailer. A trailer will be used herein as an exemplary vehicle 28. The trailer 28 can be positioned next to the grain sampling probe assembly 14. The extendable support arm portion 24 and/or the base structure portion 26 can be manipulated to position the grain probe portion 22 over the particulate load or product. Furthermore, the extendable support arm portion 24 and/or the base structure portion 26 can be manipulated and to push the grain probe portion 22 into the product to retrieve a particulate sample therefrom. The grain sampling probe assembly 14 is configured to reach most locations of the exposed product in the trailer 28.

The computer 10 may be connected to a communication network 18 and one or more remote computing devices 20. The remote computing devices 20 may include, for example, a desktop computer, a laptop or tablet computer, a mobile device, or the like, or combinations thereof, configured to retrieve data updates periodically or continuously from the computer 10. The computer 10 may comprise and/or work in conjunction with application servers, database servers, file servers, mail servers, print servers, or the like, or combinations thereof. Furthermore, the computer 10 may include one or more servers, virtual servers, or combinations thereof.

The communication network 18 may provide wired and/or wireless communication between the remote computing devices 20 and the computer 10. Each of the computer 10 and remote computing devices 20 may be configured to send data to and/or receive data from network 18 using one or more suitable communication protocols, which may be the same communication protocols or different communication protocols as one another.

The communication network 18 generally allows communication between the remote computing devices 20 and the computer 10. For example, the computer 10 may, upon request, periodically and/or continuously push or otherwise provide new or updated data regarding grain probing/sampling operations to the remote computing devices 20 over the communication network 18.

Network 18 may include one or more telecommunication networks, nodes, and/or links used to facilitate data exchanges between one or more devices and may facilitate a connection to the Internet for devices configured to communicate with network 18. The communication network 18 may include local area networks, metro area networks, wide area networks, cloud networks, the Internet, cellular networks, plain old telephone service (POTS) networks, and the like, or combinations thereof.

The communication network 18 may be wired, wireless, or combinations thereof and may include components such as modems, gateways, switches, routers, hubs, access points, repeaters, towers, and the like. The remote computing devices 20 and computer 10 may connect to the communication network 18 either through wires, such as electrical cables or fiber optic cables, or wirelessly, such as radio frequency (RF) communication using wireless standards such as cellular 2G, 3G, 4G or 5G, Institute of Electrical and Electronics Engineers (IEEE) 802.11 standards such as WiFi, IEEE 802.16 standards such as WiMAX, Bluetooth™, or combinations thereof. In aspects in which network 18 facilitates a connection to the Internet, data communications may take place over the network 18 via one or more suitable Internet communication protocols. For example, network 18 may be implemented as a wireless telephony network (e.g., GSM, CDMA, LTE, etc.), a Wi-Fi network (e.g., via one or more IEEE 802.11 Standards), a WiMAX network, a Bluetooth network, etc.

The computer 10 generally retains electronic data and may respond to requests to retrieve data, as well as to store data. The computer 10 may be configured to include or execute software, such as file storage applications, database applications, email or messaging applications, web server applications, and/or machine vision software or the like.

Figure 3:
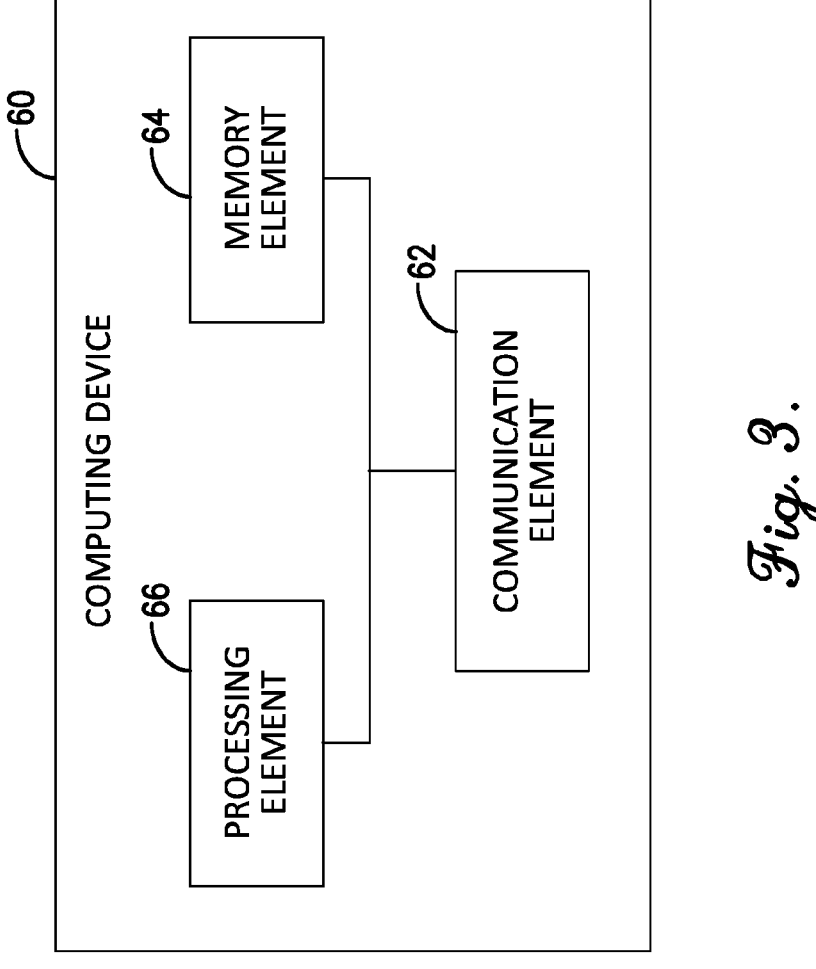
FIG. 3 is an example configuration of a computing device for use in the system shown in FIG. 1.

FIG. 3 is an example configuration of a computing device 60, such as the computer 10, the PLC 12, and/or the remote computing devices 20 (each shown in FIG. 1), for use in the autonomous grain probing system 8 (shown in FIG. 1). The computing device 60 may broadly include a communication element 62, a memory element 64, and a processing element 66.

The communication element 62 generally allows communication with external systems or devices, including the communications network 18, such as via wireless communication and/or data transmission over one or more direct or indirect radio links between devices. The communication element 62 may include signal or data transmitting and receiving circuits, such as antennas, amplifiers, filters, mixers, oscillators, digital signal processors (DSPs), and the like. The communication element 62 may establish communication wirelessly by utilizing RF signals and/or data that comply with communication standards such as cellular 2G, 3G, or 4G, WiFi, WiMAX, Bluetooth™ and the like, or combinations thereof. In addition, the communication element 62 may utilize communication standards such as ANT, ANT+, Bluetooth™ low energy (BLE), the industrial, scientific, and medical (ISM) band at 2.4 gigahertz (GHz), or the like.

Alternatively, or in addition, the communication element 62 may establish communication through connectors or couplers that receive metal conductor wires or cables which are compatible with networking technologies, such as ethernet. In certain embodiments, the communication element 62 may also couple with optical fiber cables. The communication element 62 may be in communication with the corresponding processing element 66 and the memory element 64, via, e.g., wired or wireless communication.

The memory element 64 may include electronic hardware data storage components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 64 may be embedded in, or packaged in the same package as, the corresponding processing element 66. The memory element 64 may include, or may constitute, a "computer-readable medium." The memory element 64 may store the instructions, code, code segments, software, firmware, programs, applications, apps, modules, agents, services, daemons, or the like that are executed by the processing elements, including—in the case of the processing element 66 and the memory element 64 of the computer 10—the machine vision software or the like. The memory element 64 may also store settings, data, documents, sound files, photographs, movies, images, databases, and the like, including the items described throughout this disclosure.

The processing element 66 may include electronic hardware components such as processors. The processing element 66 may include digital processing unit(s). The processing element 66 may include microprocessors (single-core and multi-core), microcontrollers, digital signal processors (DSPs), field-programmable gate arrays (FPGAs), analog and/or digital application-specific integrated circuits (ASICs), or the like, or combinations thereof. The processing element 66 may generally execute, process, or run instructions, code, code segments, software, firmware, programs, applications, apps, modules, agents, processes, services, daemons, or the like, including—in the case of processing element 66 of the computer 10—the machine vision software described throughout this disclosure. The processing element 66 may also include hardware components such as finite-state machines, sequential and combinational logic, and other electronic circuits that can perform the functions necessary for the operation of the current invention. The processing element 66 may be in communication with the other electronic components through serial or parallel links that include address busses, data busses, control lines, and the like.

Through hardware, software, firmware, or combinations thereof, the processing element 66 may be configured or programmed to perform the functions described herein below.

Exemplary Computer-Implemented Method

Figure 4:
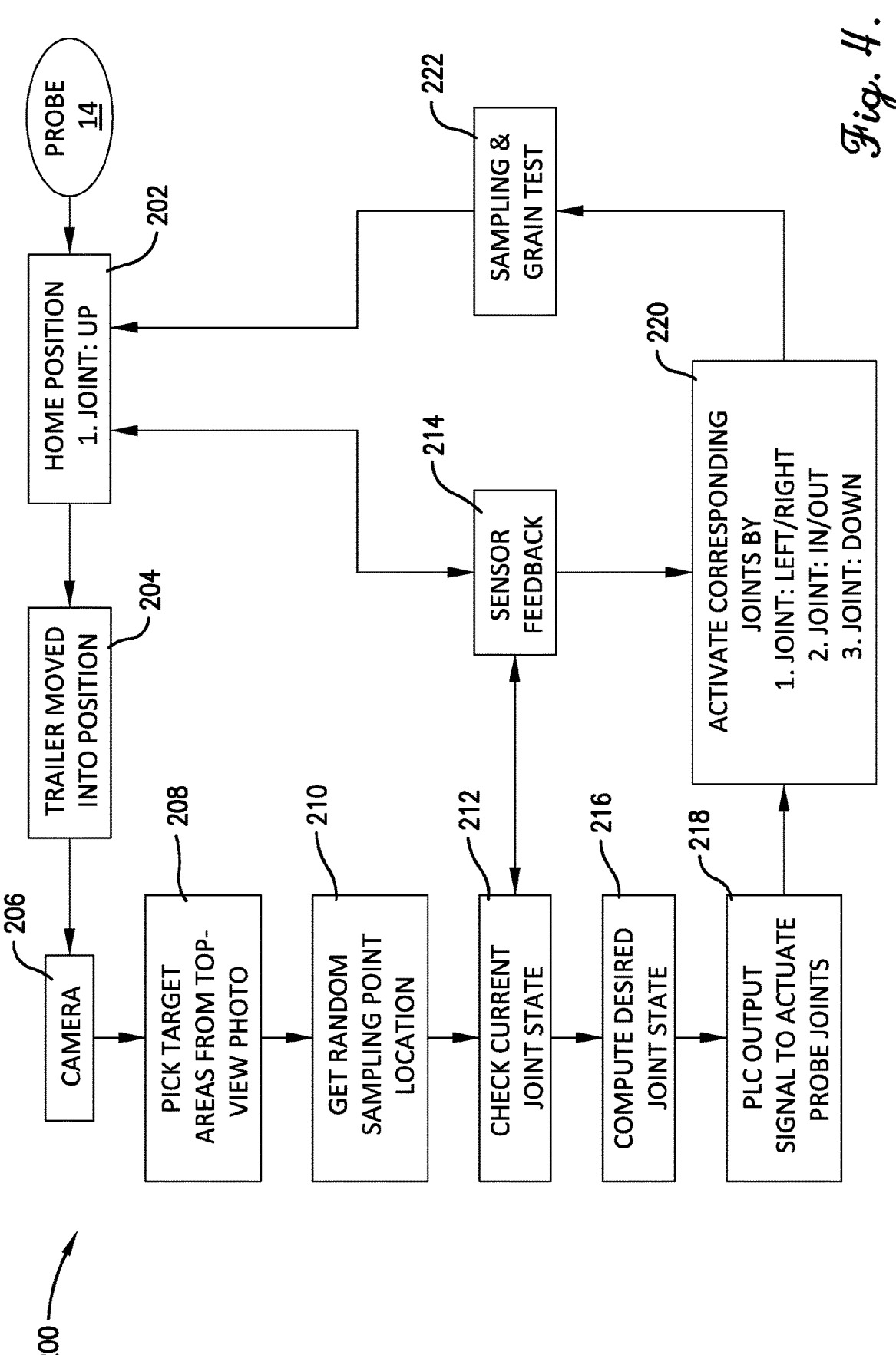
FIG. 4 depicts a workflow of the autonomous grain probing system shown in FIG. 1.

FIG. 4 depicts a workflow of the autonomous grain probing system 8, listing operations of an exemplary computer-implemented method 200 for autonomously sampling a grain product contained, for example, in the trailer 28 of a truck. The steps may be performed in the order shown in FIG. 4, or they may be performed in a different order. Furthermore, some steps may be performed concurrently as opposed to sequentially. In addition, some steps may be optional.

The computer-implemented method 200 is described below, for ease of reference, as being executed by exemplary devices and components introduced with the embodiments illustrated in FIGS. 1, 2, and 4. For example, the operations of the computer-implemented method 200 may be performed by the computer 10, the grain sampling probe assembly 14, and the optical sensor 16 through the utilization of processors, transceivers, hardware, software, firmware, or combinations thereof. However, a person having ordinary skill will appreciate that responsibility for all or some of such actions may be distributed differently among such devices or other computing devices without departing from the spirit of the present invention. For example, the operations performed by the computer(s) 10 may be performed in whole or in part by one or more other computing devices—such as laptop or desktop computers or other personal computing devices—without departing from the spirit of the present invention.

One or more computer-readable medium(s) may also be provided. The computer-readable medium(s) may include one or more executable programs stored thereon, wherein the program(s) instruct one or more processing elements to perform all or certain of the steps outlined herein. The program(s) stored on the computer-readable medium(s) may instruct the processing element(s) to perform additional, fewer, or alternative actions, including those discussed elsewhere herein.

As depicted in FIG. 4 at step 202, the grain sampling probe assembly 14 is initially positioned in a "home" position. For example, the grain sampling probe assembly 14 may be in an up position and rotated such that the extendable support arm portion 24 is generally parallel to the trailer 28 (see FIG. 1). At step 204, a container, such as the trailer 28, is positioned for sampling (e.g., by a truck pulling the trailer 28).

At step 206, the computer 10 detects the trailer 28. More particularly, in the example embodiment, the optical sensor 16 is generally continuously scanning the probing environment and transmitting a stream of image data to the computer 10. For example, the optical sensor 16 may capture a predetermined number of frames per second (FPS), such as twenty-five (25) FPS, thirty (30) FPS, sixty (60) FPS, and the like. The frame rate of the camera may be fixed by the camera hardware or may be selected by a user. It is noted that the frame rate can be any value that enables the autonomous grain probing system 8 to function as described herein. The computer 10 analyzes the data stream from the optical sensor 16 and detects the trailer 28.

At step 208, the computer 10 performs an image processing procedure to determine one or more target areas within the boundaries of the trailer 28 for sampling. In addition, at step 210, the computer 10 determines an X and Y coordinate position (e.g., in the horizontal plane) for each of one or more sampling points within each of the identified one or more target areas. The camera view generally provides a top view of the trailer 28 to the computer 10. The areas for probing are determined, thusly, from generally a top view of the trailer 28.

More particularly, the image processing procedure includes using a plurality of machine vision algorithms and techniques to identify the one or more target areas for probing. For example, in the example embodiment, the computer 10 receives an image of the trailer 28 positioned in the probing environment, as noted at step 206. The computer 10 then performs a plurality of classification processes to identify and classify the trailer walls, any tarp supports extending between trailer walls, the ground surface of the probing environment, and/or optionally, the product (e.g., grain) contained in the trailer. Optionally, in some embodiments, the computer 10 may access a database that includes a plurality of predefined models representing various trailers/trucks and their respective geometry. Thus, if the computer 10 can identify the trailer 28 as matching a predefined model, at least some of the geometry classifications processes may not be performed.

Using binarization techniques with predefined thresholds, the computer 10 may define separate sections of the trailer 28 based on the identification of the trailer walls, tarp supports, the ground surface of the probing environment, and/or the grain contained in the trailer 28. For example, the computer 10 may implement a perspective transform to get a top view of the trailer 28 within a pre-set target area. Then the computer 10 may use k-means clustering to identify several dominant colors of the new image. Optionally, in an example, a database may contain a record of hues that generally correlate to a type of grain. After matching hues of the image colors to the database, the computer 10 may identify the grain color identifying the type of grain.

The computer 10 applies several filters to define the grain area for sampling and, as noted at step 208, generates X-Y sampling target points within the defined grain area. In one example embodiment, the computer 10 may identify a Z-axis location based on an algorithm to establish an assumed "floor" of the trailer 28. The computer 10 may then apply various geometry transformations to determine one or more three-dimensional locations of the probing environment relative to the two-dimensional image coordinates. For example, the computer 10 may assume that a floor of the trailer 28 is lowest near a center portion of the trailer 28 and highest near respective ends of the trailer 28. For example, the computer 10 may be programmed to assume that about a central thirty percent (30%) of a length of the trailer 28 has a floor height defined at about four feet (4 ft.) above the ground surface. Similarly, the computer 10 may be programmed to assume that the front thirty-five percent (35%) and the rear thirty-five percent (35%) of the trailer 28 has a floor height that increases linearly from the four foot (4 ft.) central portion to a height of about twelve feet (12 ft.). It is noted, however, that the floor heights noted above are exemplary only, and that any floor heights may be defined that enables the system 8 to function as described herein, while providing, for example, a desired safety margin to avoid hitting the floor of the trailer 28 with the grain probe portion 22. In an optional embodiment, the computer 10 may apply various geometry transformations to determine three-dimensional locations of the probing environment relative to the two-dimensional image coordinates, for example, by using range finder data to locate a vertical position of the defined grain areas for sampling relative to the ground surface (i.e., the horizontal plane).

The image processing is performed in four (4) basic operations: position check; clear edge; segmentation; and safety check. After the image processing is completed, the grain sampling probe assembly 14 is operated to retrieve samples of the grain from the locations in the trailer, as determined by the computer 10.

During the position check operation, the trailer walls are detected as described above. The position of the trailer 28 is then compared against predefined thresholds to determine whether the trailer is in a position that allows for probing of the grain. If the trailer 28 is in a position within the predetermined thresholds, the image processing continues.

The clear edge operation includes applying a Gaussian blur to the original image provided to the computer 10 by the optical sensor 16. The Gaussian blur is applied to smooth out the image to facilitate further operations. The computer 10 then applies k-means clustering analysis to the blurred image. It is noted that any value of k may be used that enables the image processing to operate as described herein. The computer 10 applies a color range filter to the resulting k-means analyzed image. The color range filter facilitates separating the grain portions of the image from the trailer 28, tarp support, ground, etc.

After application of the color range filter, the computer 10 than applies a bilateral filter to the image to facilitate smoothing the image further. The bilateral filter reduces noise in the image while preserving edges. Next, the computer 10 performs a morphological transform operation on the image and then executes a contour detection algorithm that detects the counters/shapes in the image that are not part of the grain.

The detected contours are used to identify the various segments of the image (i.e., trailer) that are to be used for probing. After the segments are defined, the computer 10 performs a distance transform analysis to the image. In an example embodiment, the distance transform analysis may include a gray scale transformation of the image, for example, where black may define a border of a respective segment and white may include a position within the segment that is at a maximum distance from the edges of the segment. The computer 10 defines a target area within each segment that is valid for probing. For example, based on a predefined threshold distance from an edge of respective segment, the computer defines a target area (e.g., a maximized circular area) that is valid for probing. In the example, the computer 10 defines the largest circle inscribed within each segment, based on the predetermined threshold distance.

After the computer 10 defines the target area for each defined segment, the computer 10 determines one or more probe target points within each target area based on one or more pre-defined rules, as noted at step 210. The predefined rules may be preset for the system 8 and/or user defined, for example, during initial setup of the system 8. It is contemplated that different users of the system 8 may have different standards and/or processes concerning how many times to probe a trailer, such as the trailer 28. For example, one user may want to retrieve four (4) or five (5) samples from a trailer, while another user may want to retrieve only one (1) sample per trailer or trailer compartment. Additionally, one user may only be performing simple manual grading that requires minimal sample, while another user may require more sample to split into two (2) to three (3) parts for moisture testing, cleanliness, infestation, etc. Thus, in some embodiments, the predefined rules may include, for example and without limitation: i) a minimum and/or maximum number of sample points, based on user input; and ii) a user-defined amount of sample to collect, for example, at the collection cabinet 32.

It is noted that in certain embodiments, the computer 10 may be programmed to prioritize and/or rank the one or more probe target points (e.g., highest rank being closest to the center point of the trailer where grain is typically the deepest) and then proceed in order of ranking until each of the pre-defined rule requirements are met. Alternatively, the one or more probe target points can be provided to a user of the system 8 via the computer 10, thereby allowing the user to manually select which of the one or more probe target points should be probed.

At step 212, the computer 10 checks the current position of the grain sampling probe assembly 14, for example, by retrieving sensor data (e.g., sensor values) from the rotation sensor 50 and/or the linear displacement sensors 36 and 54 (e.g., receiving sensor feedback, as depicted at block 214). The sensor data is indicative of a current state or position of the sensors. At step 216, the computer 10 then calculates a desired state or value of each of the linear and/or rotational displacement sensors 36, 50, and 54 based on the coordinate positions of one or more target areas. The desired state is indicative of a desired position of the grain probe portion 22 in a defined sampling location.

At step 218, the computer 10 transmits one or more desired position sensor values to the PLC 12. At operation 220, the PLC 12 then operates the grain sampling probe assembly 14 to move it into position based on the one or more desired position sensor values. In particular, based on the known location of the grain probe portion 22 and the identified location of sampling target points, the computer 10 provides one or more desired position sensor values to the PLC 12 for one or more of rotating the pivot tube assembly using the rotational actuator 48, raising the extendable support arm portion 24 using the linear actuator 34 to control pitch, and/or extending the extendable support arm portion 24 using the extension linear actuator 33. The linear and/or rotational displacement sensors 36, 50, and 54 provide substantially continuous positional feedback (block 214) to the PLC 12 to facilitate positioning of the grain probe portion 22.

In an example, a tip of the grain probe portion 22 may include a contact sensor 56 configured to detect contact with the grain and/or any other object. The PLC 12 may receive sensor feedback 214 from the contact sensor 56 indicating that the grain probe portion 22 contacted a hard object, such as the walls of the trailer 28, tarp support, and the like. The PLC 12 may stop the grain sampling probe assembly 14 to prevent damaging the grain probe portion 22. Further, the PLC 12 may receive feedback from the contact sensor 56, which may be indicative of the grain probe portion 22 being positioned within the grain.

At step 222, the PLC 12 may then actuate the particulate transport system 38 to retrieve and deliver a sample of the grain to the collection cabinet 32 or any other grain containment device. Additionally or alternatively, in some embodiments, the PLC 12 may first actuate a compartmentalized switch (not shown) to open a compartment of the grain probe portion 22 to capture a sample of the grain. The PLC 12 may position the grain probe portion 22 in each additional defined probe location and retrieve additional sample therefrom. After completion of the sampling operation (as indicated, for example, by a sensor mounted in the collection cabinet 32), the PLC 12 operates the grain sampling probe assembly 14 to return the grain sampling probe assembly 14 to the home position.

Probing Environment Safety System

Referring to FIG. 1, one aspect of the present invention provides a safety system to facilitate positioning a vehicle, such as the trailer 28, in the probing environment and for identifying moving persons or objects in the probing environment during operation of the system 8. The safety system may include a driver communication device 68. The driver communication device 68 is configured to present information to a driver of a vehicle towing the trailer 28. The driver communication device 68 may include a display, a plurality of light emitting diodes (LEDs), etc. The driver communication device 68 is any component capable of visually and/or auditorily conveying information to a driver.

As discussed above in method 200, the optical sensor 16 detects the vehicle and/or trailer 28. The computer 10 receives image data from the optical sensor 16, determines the vehicle's position within the probing environment and provides feedback to the driver via the driver communication device 68. For example, driver communication device 68 may provide a visual signal to the driver to stop moving the vehicle when the computer 10 determines that the vehicle is positioned within a predefined area of the probing environment.

Furthermore, during operation of the grain sampling probe assembly 14, for example, to retrieve a particulate sample from the trailer 28, the optical sensor 16 and computer 10 may detect movement within the probing environment, such as the driver's presence outside the vehicle or another person or object moving within the probing environment. The computer 10 may stop operation of the grain sampling probe assembly 14 to prevent possible injury or damage to the detected object moving within the probing environment and/or damage to the grain sampling probe assembly 14.

System Initialization

During an initialization phase of the autonomous grain probing system 8, the position of the optical sensor 16 relative to the probing environment and grain sampling probe assembly 14 is established in a three-dimensional coordinate system using any suitable calibration technique, e.g., manual measurement and entry into the memory element of the computer 10. In an example, one suitable approach to calibration includes capturing images of a checkerboard pattern having a known size and shape. The checkerboard pattern may be projected by the projector onto the ground surface of the probing environment and/or may be printed, for example, on posterboard, which is placed in the probing environment. The camera may be calibrated using one or more geometric transform algorithms to map the captured image points to the known location of the points in the probing environment.

Web Application Framework

As described above, in the example, one or more remote computing devices 20 may communicate with the computer 10 via the communications network 18. The computer 10 may include a webserver to facilitate presenting data from the probing operations to the one or more remote computing devices 20. In addition, the one or more remote computing devices 20 may provide input signals to the computer 10 for operating the grain sampling probe assembly 14. In one example, the computer 10 uses Nginx as the webserver. uWSGI is a software application running on the computer 10 to facilitate communications between the webserver and various web applications. For example, uWSGI may be used for serving Python web applications in conjunction with Nginx. The computer 10 may also implement Flask (a web framework), which is designed to support the development of web applications including web services, web resources, and web APIs. The web application framework allows a user of a remote computing device 20 to visualize various historical data associated with the autonomous grain probing system 8, visualize current operations of the autonomous grain probing system 8, and fully operate and/or calibrate the autonomous grain probing system 8 from a remote location.

Additional Considerations

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the current technology can include a variety of combinations and/or integrations of the embodiments described herein.

Although the present application sets forth a detailed description of numerous different embodiments, it should be understood that the legal scope of the description is defined by the words of the claims and equivalent language. The detailed description is to be construed as exemplary only and does not describe every possible embodiment because describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order recited or illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. The foregoing statements in this paragraph shall apply unless so stated in the description and/or except as will be readily apparent to those skilled in the art from the description.

Certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as computer hardware that operates to perform certain operations as described herein.

In various embodiments, computer hardware, such as a processor or processing element, may be implemented as special purpose or as general purpose. For example, the processor may comprise dedicated circuitry or logic that is permanently configured, such as an application-specific integrated circuit (ASIC), or indefinitely configured, such as a field-programmable gate array (FPGA), to perform certain operations. The processor may also comprise programmable logic or circuitry (e.g., as encompassed within a general-purpose processor or other programmable processor) that is temporarily configured by software to perform certain operations. It will be appreciated that the decision to implement the processor as special purpose, in dedicated and permanently configured circuitry, or as general purpose (e.g., configured by software for a special purpose) may be driven by cost and time considerations.

Accordingly, the term "processing element," "processor," and equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processor is temporarily configured (e.g., programmed), each of the processors need not be configured or instantiated at any one instance in time. For example, where the processor includes a general-purpose processor configured using software, the general-purpose processor may be configured as respective different processors at various times. Software may accordingly configure the processor to constitute a particular hardware configuration at one instance of time and to constitute a different hardware configuration at a different instance of time.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at various times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, at a later time, access the memory device to retrieve and process the stored output. Computer hardware components may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processors may be located in a single location (e.g., within a home environment, an office environment or as a server farm), while in other embodiments the processors may be distributed across a number of locations.

Unless specifically stated otherwise, discussions herein using words such as "processing," "computing," "calculating," "determining," "presenting," "displaying," or the like may refer to actions or processes of a machine (e.g., a computer with a processor and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

Although the disclosure has been described with reference to the embodiments illustrated in the attached figures, it is noted that equivalents may be employed, and substitutions made herein, without departing from the scope of the disclosure as recited in the claims.

What is claimed is:

1. An autonomous system comprising:
a particulate sampling probe assembly comprising:
    a probe portion that is moveable between a first position and a second position; and
    a sensor having a first sensor value, the first sensor value indicative of the first position;
a programmable logic controller operatively coupled to the particulate sampling probe assembly;
an optical sensor that captures image data of a predefined probing environment; and
a computer coupled in communication with the optical sensor, the programmable logic controller, and the particulate sampling probe assembly,
the computer comprising a processing element and a memory element, the memory element having computer executable instructions stored thereon that, when executed by the processing element, cause the processing element to:
    receive the image data from the optical sensor;
    detect a vehicle positioned within the predefined probing environment;
    based on the image data, determine one or more target areas within the vehicle;

determine an X coordinate position and a Y coordinate position of one or more probe target points within each of the one or more target areas;

retrieve the first sensor value from the sensor;

determine a second sensor value based on the first sensor value and the X and Y coordinate positions, the second sensor value being indicative of the second position, wherein the second position corresponds to the probe portion being positioned at the X and Y coordinate positions in one of the one or more target areas;

transmit the second sensor value to the programmable logic controller; and prioritize the one or more probe target points based on proximity of the probe target points to a center point of the vehicle.

2. The autonomous system in accordance with claim 1, wherein the determination of the X coordinate position and the Y coordinate position of the one or more probe target points is based on one or more pre-defined rules, the one or more pre-defined rules including one or more of the following:

a minimum or maximum number of probe target points; and a user-defined amount of sample to collect.

3. The autonomous system in accordance with claim 1, wherein the computer executable instructions further cause the processing element to present the one or more probe target points to a user of the computer for selection.

4. The autonomous system in accordance with claim 1, wherein the determination of the X coordinate position and the Y coordinate position of the one or more probe target points is based on one or more pre-defined rules, the one or more pre-defined rules including one or more of the following:

a minimum or maximum number of probe target points; and a user-defined amount of sample to collect.

5. The autonomous system in accordance with claim 1, further comprising after transmitting the second sensor value to the programmable logic controller, causing the programmable logic controller operating the particulate sampling probe assembly to cause the probe portion to move to the second position based on the second sensor value.

6. The autonomous system in accordance with claim 5, further comprising a particulate transport system operatively coupled to the programmable logic controller, the programmable logic controller actuating the particulate transport system after the probe portion is moved to the second position.

7. A method performed by a computer of an autonomous system, the autonomous system including a particulate sampling probe assembly, a programmable logic controller, and an optical sensor that captures image data of a predefined probing environment, the particulate sampling probe assembly including a moveable probe portion that is moveable between a first position and a second position, and a sensor having a first sensor value, the first sensor value indicative of the first position, the method comprising:

receiving image data from the optical sensor;

detecting a vehicle positioned within the predefined probing environment;

based on the image data, determining one or more target areas within the vehicle;

determining an X coordinate position and a Y coordinate position of one or more probe target points within each of the one or more target areas;

retrieving the first sensor value from the sensor;

determining a second sensor value based on the first sensor value and the X and Y coordinate positions, the second sensor value being indicative of the second position, wherein the second position corresponds to the probe portion being positioned at the X and Y coordinate positions in one of the one or more target areas;

transmitting the second sensor value to the programmable logic controller; and prioritizing the one or more probe target points based on proximity of the probe target points to a center point of the vehicle.

8. The method in accordance with claim 7, wherein determining an X coordinate position and a Y coordinate position of the one or more probe target points is based on one or more pre-defined rules, the one or more pre-defined rules including one or more of the following:

a minimum or maximum number of probe target points; and a user-defined amount of sample to collect.

9. The method in accordance with claim 7, further comprising presenting the one or more probe target points to a user of the computer for selection.

10. The method in accordance with claim 7, wherein determining an X coordinate position and a Y coordinate position of the one or more probe target points is based on one or more pre-defined rules, the one or more pre-defined rules including one or more of the following:

a minimum or maximum number of probe target points; and a user-defined amount of sample to collect.

11. The method in accordance with claim 7, further comprising after transmitting the second sensor value to the programmable logic controller, operating, by the programmable logic controller, the particulate sampling probe assembly and moving the probe portion to the second position based on the second sensor value.

12. The method in accordance with claim 11, further comprising actuating by the programmable logic controller, a particulate transport system after the probe portion is moved to the second position.

13. A non-transitory computer-readable medium having stored thereon computer executable instructions that when executed by a processor of computer, cause the processor to:

receive image data from an optical sensor, the image data captured of a predefined probing environment;

detect a vehicle positioned within the predefined probing environment;

based on the image data, determine one or more target areas within the vehicle;

determine an X coordinate position and a Y coordinate position of one or more probe target points within each of the one or more target areas;

retrieve a first sensor value from a sensor of a particulate sampling probe assembly, the particulate sampling probe assembly including a moveable probe portion that is moveable between a first position and a second position, the first sensor value indicative of the first position;

determine a second sensor value based on the first sensor value and the X and Y coordinate positions, the second sensor value being indicative of the second position, wherein the second position corresponds to the probe portion being positioned at the X and Y coordinate positions in one of the one or more target areas;

transmit the second sensor value to a programmable logic controller; and prioritize the one or more probe target points based on proximity of the probe target points to a center point of the vehicle.

14. The non-transitory computer-readable medium in accordance with claim 13, wherein the determination of the one or more probe target points is based on one or more pre-defined rules, the one or more pre-defined rules including one or more of the following:

a minimum or maximum number of probe target points; and a user-defined amount of sample to collect.

15. The non-transitory computer-readable medium in accordance with claim 13, wherein the computer executable instructions further cause the processor to present the one or more probe target points to a user of the computer for selection.

16. The non-transitory computer-readable medium in accordance with claim 13, wherein the determination of the one or more probe target points is based on one or more pre-defined rules, the one or more pre-defined rules including one or more of the following:

a minimum or maximum number of probe target points; and a user-defined amount of sample to collect.

17. The non-transitory computer-readable medium in accordance with claim 13, wherein the computer executable instructions further cause the processor to operate, by a programmable logic controller, the particulate sampling probe assembly and move the probe portion to the second position based on the second sensor value.

\* \* \* \* \*